United States Patent [19]

Wegner et al.

[11] Patent Number: 4,670,397
[45] Date of Patent: Jun. 2, 1987

[54] FERMENTATION APPARATUS

[75] Inventors: Eugene H. Wegner; Harold R. Hunt, both of Bartlesville, Okla.

[73] Assignee: Phillips Petroleum Company, Bartlesville, Okla.

[21] Appl. No.: 826,424

[22] Filed: Feb. 5, 1986

[51] Int. Cl.⁴ ............................................. C12M 1/02
[52] U.S. Cl. ........................... 435/289; 435/243; 435/314; 435/315; 435/316; 435/804; 165/109.1
[58] Field of Search ............... 435/243, 246, 247, 284, 435/289, 313, 315, 316, 804, 812, 314; 165/109.1, 163

[56] References Cited

U.S. PATENT DOCUMENTS

| Re. 30,543 | 3/1981 | Hitzman | 435/246 |
|---|---|---|---|
| 2,983,652 | 2/1959 | Baerfuss | 435/314 |
| 3,384,491 | 5/1968 | Guenther et al. | 99/9 |
| 3,460,810 | 8/1969 | Mueller | 259/96 |
| 3,625,834 | 12/1971 | Muller | 435/243 |
| 3,809,618 | 6/1972 | Muller | 435/289 |
| 3,847,750 | 11/1974 | Ridgway | 435/289 |
| 3,887,432 | 6/1975 | Cawthorne | 435/44 |
| 3,957,585 | 5/1976 | Malick | 435/243 |
| 3,962,042 | 6/1976 | Malick | 435/314 |
| 3,977,946 | 8/1976 | Malick | 435/289 |
| 3,978,918 | 9/1976 | Nagatomo | 165/109 |
| 3,982,998 | 9/1976 | Hitzman | 435/246 |
| 3,984,286 | 10/1976 | Malick | 435/314 |
| 3,985,622 | 10/1976 | Hawkins | 435/289 |
| 3,986,934 | 10/1976 | Müller | 435/812 X |
| 4,003,160 | 1/1977 | Muller | 47/58 |
| 4,019,962 | 4/1977 | Allen | 435/289 |
| 4,036,699 | 7/1977 | Quigg | 435/289 |
| 4,085,007 | 4/1978 | Hawkins | 435/247 |
| 4,097,339 | 6/1978 | Marwil | 435/289 |
| 4,169,010 | 9/1979 | Marwil | 435/247 |
| 4,224,414 | 9/1980 | Vanderveen | 435/313 |
| 4,264,740 | 4/1981 | Christ | 435/289 |
| 4,414,329 | 11/1983 | Wegner | 435/68 |
| 4,426,450 | 1/1984 | Donofrio | 435/243 |
| 4,588,024 | 5/1986 | Murray et al. | 165/109.1 |

FOREIGN PATENT DOCUMENTS 682520 10/1930 Fed. Rep. of Germany.
681847 10/1939 Fed. Rep. of Germany.

OTHER PUBLICATIONS

Platecoil product literature, Trantler Manufacturing, Inc., Lansing, Mich.
Panelcoil product literature, Dean Products, Inc., Brooklyn, N.Y.
Chemical and Engineering News, pp. 21-22, (8/1/83).
Provesta Corporation product brochure entitled, "Provesteen".

Primary Examiner—Margaret A. Focarino
Attorney, Agent, or Firm—S. E. Reiter

[57] ABSTRACT

Fermentation apparatus useful for conducting aerobic fermentations of microbial cells, particularly at high productivities, is disclosed.

21 Claims, 6 Drawing Figures

FERMENTATION APPARATUS

This invention relates to fermentation apparatus suitable for conducting aqueous, aerobic fermentation processes. In one aspect, the invention relates to fermentation apparatus useful for growing microorganisms at high productivity.

BACKGROUND

Worldwide food shortages over the past several years have encouraged the research and development of methods and apparatus for producing high quality, low cost microbial protein, i.e., single cell protein (SCP), to alleviate the food shortages.

Efforts to relieve the worldwide shortages of protein have included various biosynthesis processes. Biologically produced single cell protein (SCP) has been obtained by the growth of a variety of microorganisms including bacteria, yeast and fungi on a variety of carbon-containing substrates. Petroleum hydrocarbons have been employed as carbon and energy sources, but have faced practical difficulties due to their lack of water solubility, and their high consumption of oxygen required for microbial conversion. Other feedstocks used include oxygenated hydrocarbon derivatives due to the inherent water solubility of such feedstocks. Oxygenated hydrocarbon derivatives are commonly employed because of their ease of handling since microbial conversion processes are essentially conducted under aqueous conditions.

Aerobic microbial conversions are highly exothermic oxidation reactions which demand large quantities of molecular oxygen, and which produce large quantities of heat. The heat must be removed continuously and consistently, at the risk of overheating the system. Overheating of the system can cause the death of the microorganisms, or at least cause severe limitations on growth of the microorganisms as temperatures rise, and hence cause severe reductions in fermentor efficiencies. In addition, sufficient supplies of molecular oxygen are necessary to maintain high fermentation efficiencies.

To maintain high fermentation efficiencies in commercial fermentations, oxygen is supplied to the culture media as a molecular oxygen-containing gas free of any stray microorganisms under conditions to provide maximum contact of the oxygen with the culture media. This is done to dissolve as much oxygen in the aqueous media as possible.

High oxygen transfer rates have been achieved heretofore by conducting a fermentation process as a foam-type process. The use of foam assists in achieving a high surface area for contact between the liquid phase and the gas phase. Foam also allows one to obtain a high rate of oxygen transfer from the gas phase into the aqueous phase, and at the same time assists in obtaining a good rate of removal of carbon dioxide, a natural consequence of aerobic fermentation processes. Carbon dioxide which is transferred from the aqueous medium to the gas phase is then exhausted for such use as may be suitable.

There is a continuing need for improved apparatus suitable for conducting aerobic fermentation processes with high oxygen transfer rates, i.e., apparatus capable of providing effective contact between the aqueous medium and the oxygen-containing gas phase. At the same time, an apparatus is desired which is basically straightforward in construction, economical to manufacture and maintain, and yet well adapted for its intended use.

Research has been conducted for processes which provide for growing SCP at high productivities, e.g., to high cell densities as disclosed in U.S. Pat. No. 4,414,329 by Wegner (assigned to Phillips Petroleum Company). High productivity may be defined as fermentor productivity of at least 8 grams per liter per hour (g/L/hr) based on the volume of ungassed broth. High cell density may be defined as the growth of microbial cells (i.e., typically bacteria and yeast) in unusually high concentrations (i.e., $\sim \geq 50$ g/L for bacteria and $\sim \geq 80$ g/L for yeast). The obvious advantage, of course, of growing SCP to high productivities is that there is provided a greater quantity of food source from a given fermentor volume for a given period of time.

As a consequence of the development of high productivity fermentation processes, there is an even greater need for improved aerobic fermentation apparatus for the continuous production of microbial cells at high productivities. A well designed apparatus will, of course, optimize several features or properties of the fermentation apparatus. For example, extremely high heat removal and oxygen transfer capabilities are necessary. Lower power inputs to operate the fermentation apparatus while still achieving the above desired ends is also highly desirable. Finally, a fermentation vessel which does not require an anti-foaming agent for effective control of a high cell density fermentation process would provide a tremendous advantage. This is because the presence of anti-foaming agent causes not only reduced oxygen transfer but also results in an increased density of fluid mass, which in turn requires increased power input. Moreover, anti-foaming agent ends up in the final product, which inclusion may be undesireable.

Thus, a fermentation apparatus which can be used in aqueous, aerobic fermentation process, particularly high productivity processes, and that maximizes and/or minimizes the above-mentioned features, as appropriate, is highly desirable.

OBJECTS OF THE INVENTION

It is an object of this invention, therefore, to provide a novel fermentation apparatus which can be efficiently and effectively used in aqueous, aerobic fermentation processes.

Another object of the present invention is a novel fermentation apparatus suitable for use in aqueous, aerobic high productivity fermentation processes.

Other aspects, objects, and advantages will be apparent from the specification, the drawings, and the appended claims.

STATEMENT OF THE INVENTION

In accordance with the present invention, we have discovered an apparatus suitable for use in any aqueous, aerobic fermentation process, which apparatus comprises a fermentor vessel shell having heat exchange means disposed therein such that the heat exchange means is specifically oriented within the fermentor vessel both with respect to the angle of repose of the heat exchange means relative to the axis of the vessel and with respect to the volume of the vessel occupied by the heat exchange means. The fermentor vessel of our invention is further equipped with an agitation means which is positioned within the unobstructed zone of the vessel, i.e., that portion of the vessel not occupied by the heat exchange means. The spatial relationship between the bottom-most impeller of the heat exchange means and the inlet means for the introduction of gas to the vessel is also specified to fall within a certain range. In addition, our invention fermentation vessel is equipped with inlet means for introduction of carbon and energy source and nutrient media-as well as outlet means for removal of product and removal of off-gases. As a result of the combination of components employed on our novel fermentation vessel, as well as the specified geometric relationships therebetween, our invention apparatus is quite efficient for fermentation processes because it provides both high heat exchange and high oxygen transfer capabilities.

Our invention is particularly useful for conducting high cell density fermentation processes, such as for example, the fermentation process disclosed in U.S. Pat. No. 4,414,329 by Wegner and assigned to Phillips Petroleum Company.

DETAILED DESCRIPTION OF THE INVENTION

One advantage of high productivity fermentation processes, such as, for example, those disclosed by Wegner in U.S. Pat. No. 4,414,329, is the simple treatment required for workup of the fermentation effluent. Thus, effluent from the fermentor can be passed directly to a heat treatment step, and thereafter passed directly to drying means, e.g., a spray drier, from which dry product is obtained. The invention apparatus is well-suited for carrying out high productivity fermentation processes, as will become apparent from the following discussion.

One embodiment of the fermentation vessel of the present invention will now be described in greater detail with reference to the figures.

The general dimensions of fermentation vessel 10 are selected such that the ratio of length to diameter is generally in the range of about 0.1 up to 10:1. Preferably, the ratio of length to diameter of the fermentation vessel is in the range of about 0.3 up to 5:1, with the ratio of length to diameter most preferably falling in the range of about 1 up to 4:1.

Figure 1:
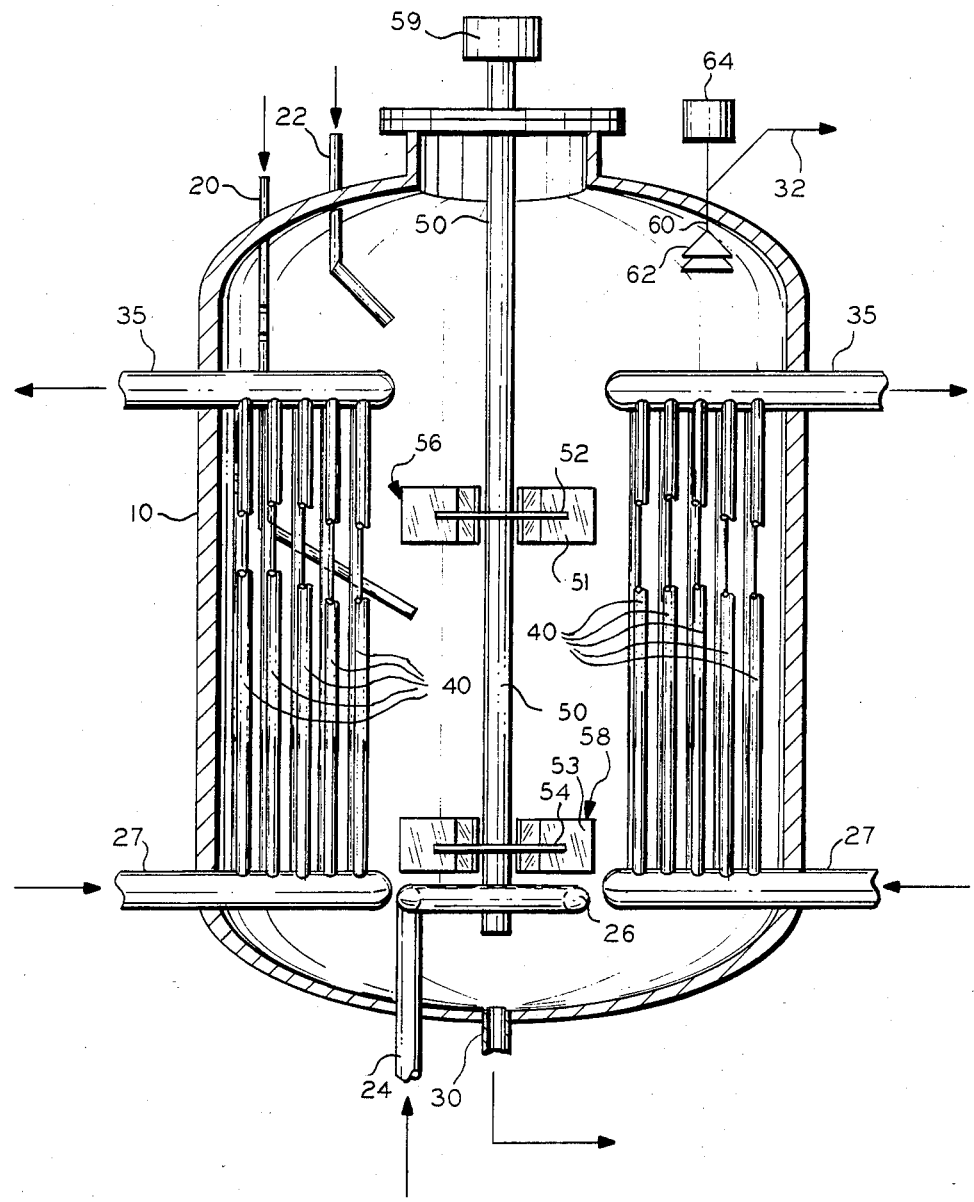
FIG. 1 is a cutaway view of a fermentation vessel designed in accordance with one embodiment of the present invention.

Heat exchange fluid is provided to parallel tubes 40 via inlets 27, as shown in FIG. 1. Heat exchange fluid passes through inlets 27 which distributes heat exchange fluid through tubes 40. After heat exchange fluid passes through tubes 40, it is collected and discharged via outlet 35. At least two baffles, each comprising a first and second tube header (reference numerals 27 and 35) and parallel tubes 40, are employed in the invention fermentation vessel. As illustrated in FIG. 1, each baffle comprises a bundle of parallel tube rows. The tubes 40 in each baffle are typically about 25-90% of the length of the straight portion of the vessel, not including the domed vessel heads.

Those of skill in the art recognize that a widely varied number of cooling baffles can be employed, depending on the size of the cooling baffles, the number of tubes per baffle, etc. Up to as many as 30 baffles per fermentation vessel can be employed, with in the range of about 4 up to 24 baffles per fermentation vessel being preferred.

As one alternative, the baffles can be assembled as a stacked array of a plurality of baffles, each of which is shorter than the total length of baffle assembled in the fermentor vessel. By assembling the baffles as a stacked array of short segments, with a total length equivalent to the 25-90% of total straight vessel length called for above where the cooling baffles were assembled as a contiguous parallel tube arrangement, shorter tubes which are more resistant to vibration and other stresses during the fermentation process can be used. Those of skill in the art recognize that up to about 10 cooling baffle assemblies can be stacked to provide the required cooling capacity which occupies about 25-90% of the straight vessel length of the fermentor vessel.

Figure 5:
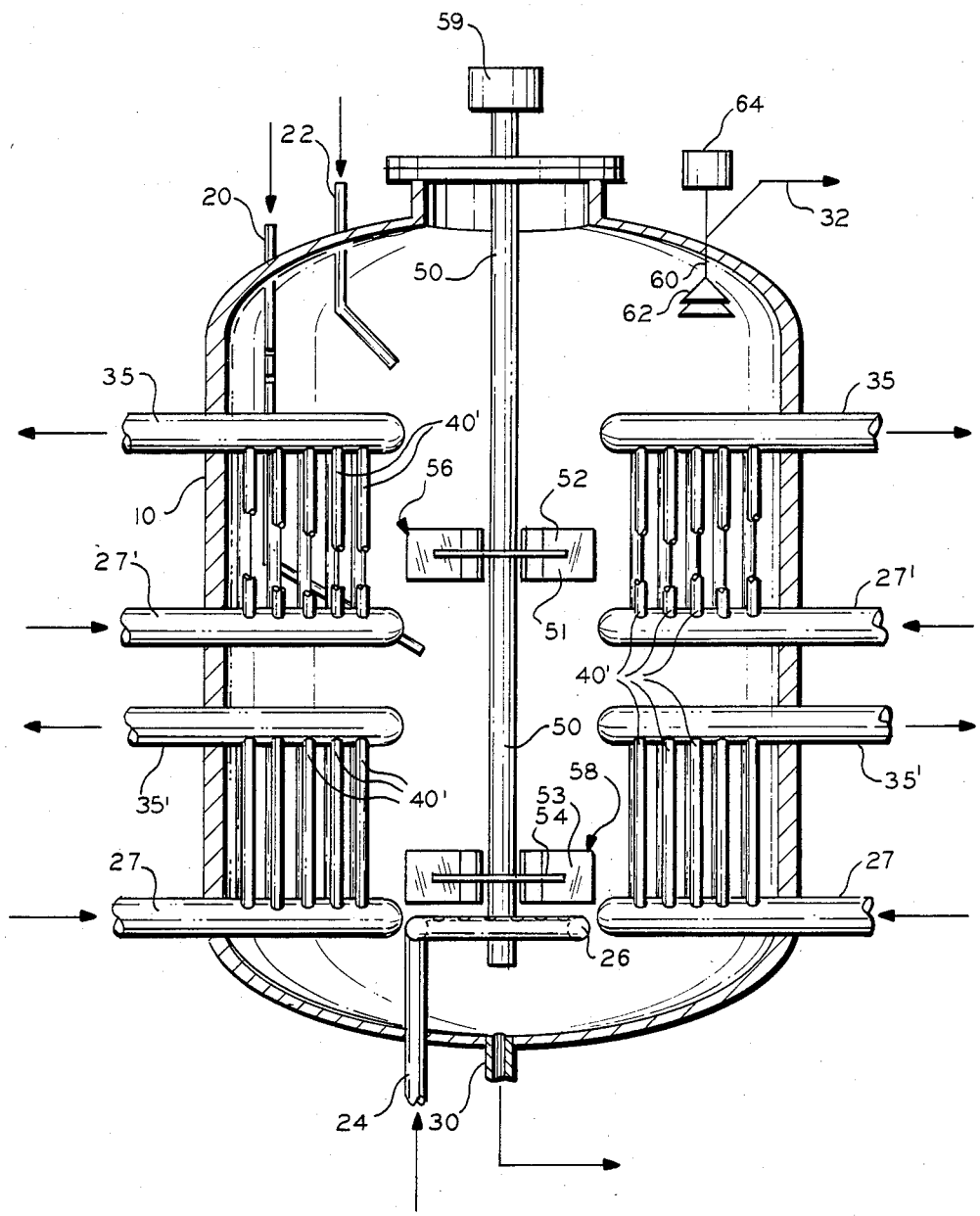
FIG. 5, is a cutaway view of a fermentation vessel designed in accordance with yet another embodiment of the present invention.

One embodiment of this stacked array alternative is illustrated in FIG. 5.

The number of cooling baffle assemblies employed will, to some extent, be a function of the overall dimensions of the fermentor vessel, as well as the materials of construction of the cooling tubes, i.e., the resistance of the materials of construction to stress, and general engineering considerations. While the cooling baffles shown in FIG. 1 are one contiguous assembly, baffles constructed of two up to about four stacked cooling baffle assemblies are preferred due to the improved resistance of such assemblies to the stresses to which they are subjected during the fermentation process.

Figure 2:
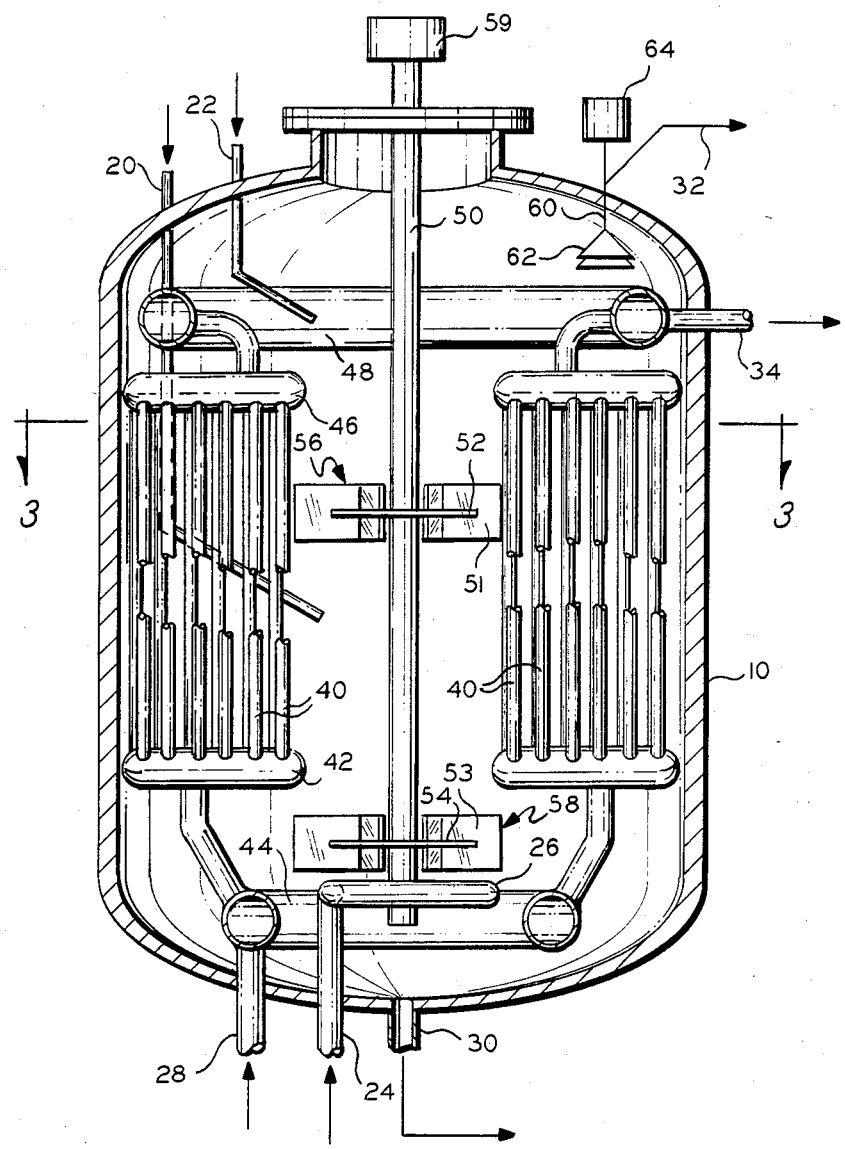
FIG. 2 is a cutaway view of a fermentation vessel designed in accordance with another embodiment of the present invention.

As another alternative, the heat exchange fluid is provided to the parallel tubes 40 via inlet 28, illustrated in FIG. 2. Heat exchange fluid passes through inlet 28 to main inlet header 44, also referred to as a supply header, which distributes heat exchange fluid to the baffles via first tube headers 42, which then distribute heat exchange fluid through parallel tubes 40. After heat exchange fluid passes through parallel tubes 40, it is initially collected in second tube headers 46, then passed to main outlet header 48, also referred to as a collection header, and finally discharges via outlet 34. Those of skill in the art recognize that the main inlet and main outlet headers can be positioned outside the vessel itself, instead of being positioned within the fermentation vessel as shown.

Figure 3:
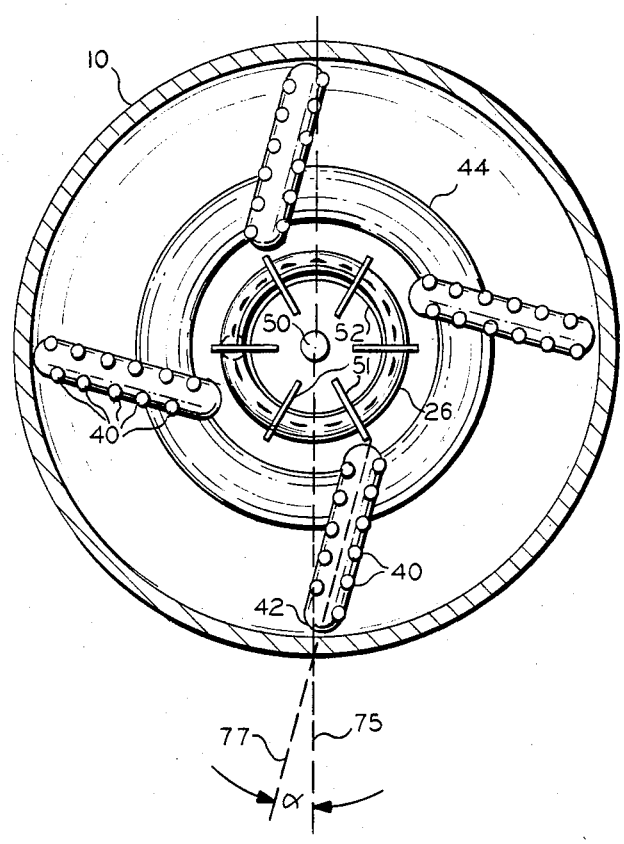
FIG. 3 is a sectional view of the fermentation vessel shown in FIG. 2.

Greater detail on the construction of the tube baffles is provided in FIG. 3, which is a section view of the embodiment shown in FIG. 2. Each tube baffle can be constructed of one up to six parallel rows of tubes, with 1 up to 4 parallel rows of tubes preferred. Each parallel row of tubes consists broadly of about 4 up to 100 parallel tubes, with the actual number of tubes employed varying as a function of tube diameter, vessel size, and the like. As illustrated in FIG. 3, it is preferred that the adjacent tubes within each row be separated by in the range of about 0.5 up to 4 tube diameters. When more than one row of parallel tubes is employed per tube baffle, it is preferred that the adjacent rows of tubes be offset one from another and separated by in the range of about 0.5 up to 4 tube diameters in order to provide maximum exposure of cooling surface with minimum resistance to fluid flow in the fermentation vessel.

As further detailed in FIG. 3, each tube bundle is positioned in the vessel at some angle, α, with respect to the axis of the fermentation vessel itself. The angle α is designated in FIG. 3 as the angle between the radial projection from the longitudinal axis of vessel 10 (reference 75) to the point where the longitudinal axis of the parallel row of tubes which make up the tubing bundle (reference 77) intersects the outer vessel diameter. In accordance with the present invention, α can range from about 5 to about 30 degrees and is preferably maintained in the range of about 10 up to 20 degrees.

As further illustrated in FIG. 3, the baffles are positioned within the fermentation vessel so as to define an inner heat exchange diameter and an outer heat exchange diameter. The inner heat exchange diameter defines an unobstructed zone which occupies in the range of about 30 up to 60% of the total internal fermentor vessel diameter. The agitation means is then positioned within this unobstructed zone, as further detailed below. The outer heat exchange diameter is no greater than the inner diameter of the fermentor vessel, and preferably is maintained within the range of about 90 up to about 98% of the total internal vessel diameter.

Figure 4:
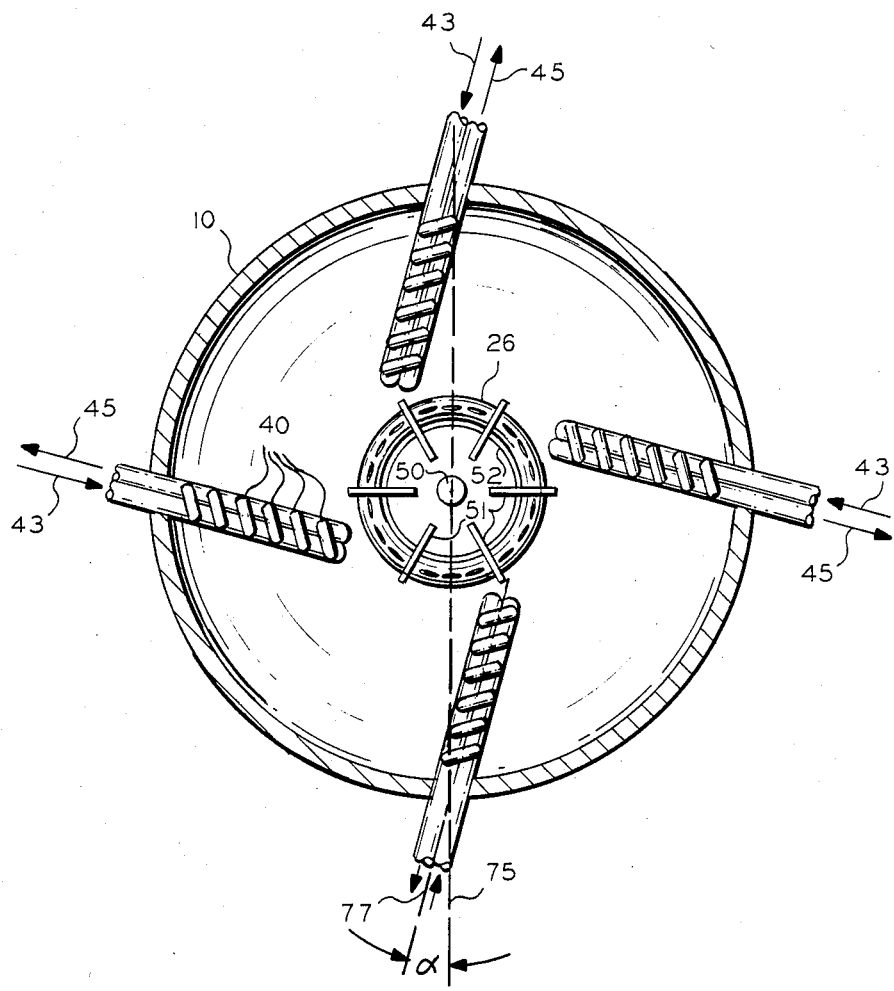
FIG. 4 is an overhead view of an alternate embodiment of the fermentation vessel designed in accordance with the present invention.

As yet another alternative embodiment, FIG. 4 illustrates the baffles as being constructed of parallel tubes wherein each tube has at least one U-shape bend such that a longer continuous flow of heat exchange fluid is accomplished than with the embodiments illustrated in FIGS. 1–3 where heat exchange fluid merely travels one baffle length before being discharged. In the embodiment shown in FIG. 4, increased heat exchange efficiency can be achieved because a higher velocity of heat exchange fluid is achieved, as well as a greater pressure drop from heat exchanger inlet to outlet. Because of the U-shape bends in the parallel tubes 40, inlet means 43 and outlet means 45 can be positioned at the same level (i.e., top or bottom) of the fermentor, rather than the upper-lower arrangement illustrated for the embodiments of FIGS. 1 and 2.

Vessel 10, as illustrated in FIGS. 1 and 2, is equipped with shaft 50 which is driven by drive means 59. Shaft 50 is shown fitted with two impellers, 56 and 58. Impellers 56 and 58 are constructed of disc 52 and 54, respectively, on which a plurality of blades 51 and 53, respectively, are mounted. Those of skill in the art recognize that a greater number of impellers can be employed, depending on vessel height, width, the dimensions of the heat exchange means, etc. In accordance with the present invention, up to about 12 impellers can be employed, with up to 8 impellers being preferred. As shown in FIGS. 1 and 2, it is preferred that the bottom-most impeller be positioned in close proximity to sparger 26, to facilitate oxygen transfer in the fermentation fluid. By the term "close proximity", it is meant that the bottom-most impeller and the sparger are positioned within about ½ to 1/10 impeller diameters from one another.

The additional 1–11 impellers employed on shaft 50 can be positioned with respect to one another in a variety of relative orientations. For ease of mounting on stirring shaft 50, multiple impellers can be spaced equally along the shaft, with the uppermost impeller being positioned at about 60 percent of the vessel height, as shown in FIGS. 1 and 2 for impeller 56.

Impeller 56 is shown in greater detail in FIG. 3. It is seen that the impeller contains a plurality of blades 51. While disc 52 is shown as containing 6 blades, those of skill in the art recognize that discs having mounted thereon from about 2 up to 12 blades will function suitably in the practice of the present invention. In addition, those of skill in the art recognize that the blades 51 can be mounted on the disc 52 in a variety of ways, e.g., with blades 51 mounted both perpendicular to the plane of the disc and on a radial projection from the vertical axis of the disc, or, alternatively, the blades 51 can be mounted on the disc 52 oriented at some angle with respect to the axis of the disc. Alternatively, impeller designs other than the specific design illustrated herein, can be employed, such as, for example, axial flow impellers, marine type propellers, and the like.

In a preferred embodiment, the bottom-most impeller 58 will be equipped with a plurality of blades which are oriented perpendicular to the plane of the disc, while the additional impellers other than the bottom-most impeller be of the same configuration or of other impeller types as are known in the art.

The upper limit as to impeller diameter is defined by the inner diameter of the heat exchange means. An impeller diameter which approaches this upper limit will provide the maximum amount of mixing per impeller. It is preferred that the impeller diameter not be smaller than about 20% of the total internal vessel diameter, and generally the impeller diameter will not exceed about 40% of the total internal vessel diameter. Preferably, an impeller diameter of about ¼ to ⅓ of the total internal vessel diameter will be employed.

In an alternate embodiment of the present invention, vessel 10 is equipped with substantially the same elements as illustrated in FIGS. 1 and 2, except the drive means for shaft 50 is located at the bottom of the fermentation vessel. Thus, the fermentation vessel for this alternative embodiment, one variation of which is set forth in FIG. 6, is referred to as a bottom drive fermentor while vessel 10 as illustrated in FIGS. 1 and 2 is referred to as a top drive fermentor.

Figure 6:
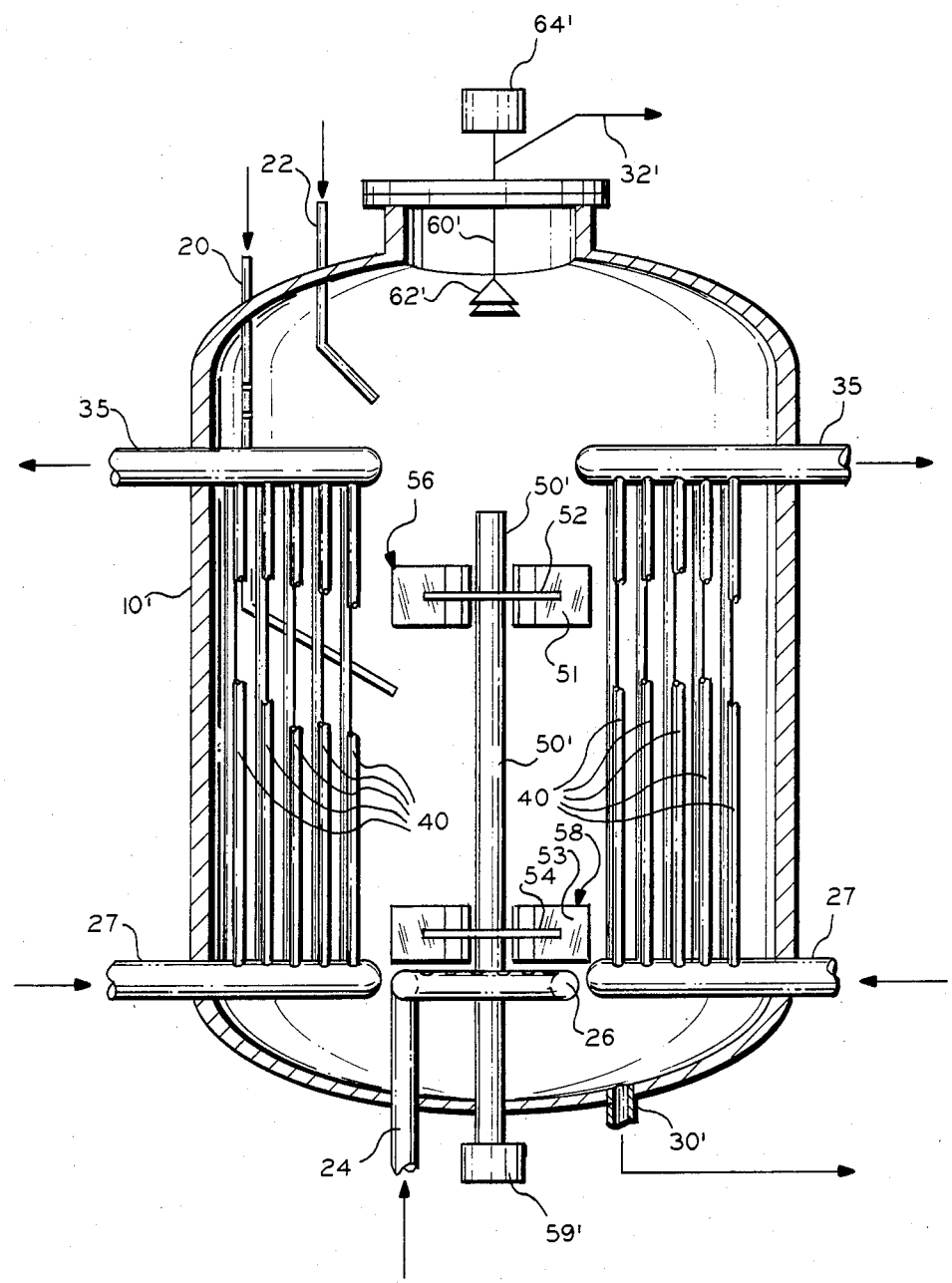
FIG. 6, is a cutaway view of a fermentation vessel designed in accordance with still another embodiment of the present invention.

As a result of the repositioning of the stirring shaft 50 and drive means 59 in the bottom drive embodiment, several changes in the positioning of other elements of the fermentation vessel illustrated in FIG. 6 are made possible. For example, outlet 30 of the fermentation vessel 10 must now be offset from the bottom center of the vessel, in contrast to the location of analogous effluent removal means 30 of vessel 10. As a result of the repositioning of shaft 50, foam breaker assembly comprising elements 60, 62 and 64 can be repositioned to a more central location at the upper most portion of the fermentation vessel, relative to the positioning of the foam breaker assembly in vessel 10 as illustrated in FIGS. 1 and 2. The remaining features of the bottom drive fermentation vessel illustrated in FIG. 6 are comparable to the components of top drive vessel described with reference to FIGS. 1 and 2.

As shown in FIGS. 1 and 2, fermentation vessel 10 is also provided with first inlet 20 and second inlet 22, as well as gas inlet 24. While vessel 10 is illustrated with the two inlets 20 & 22, those of skill in the art recognize that all feed to the fermentor could be introduced via only one inlet means or a plurality of inlet means, wherein various feed components are separately introduced. For example, for many fermentation processes, it is desirable to introduce the nutrient media and the carbon and energy source as separate feed streams, so vessel 10 is shown in FIGS. 1 and 2 in a preferred embodiment equipped with the two separate inlet means 20 and 22. While inlets 20 and 22 are illustrated with one discharge port each, those of skill in the art recognize that more dispersed introduction of feed can be achieved by employing inlets having multiple discharge ports. In addition, it is readily recognized by those of skill in the art that the inlet ports can be conveniently located at various positions about the fermentation vessel, frequently being positioned as dictated by considerations of engineering expediency.

Inlet 24 is used to introduce oxygen and optionally the nitrogen source to the fermentation vessel. Gas introduced via inlet 24 enters the fermentation vessel through sparger 26. The sparger is positioned symmetrically in the fermentor vessel with respect to the longitudinal axis of the fermentor vessel and has a face side containing a plurality of holes therein. As mentioned earlier, the diameter of the sparging means is no greater than the diameter of the bottom-most impeller under which the face side of the sparger is closely positioned.

As a result of the method of gas introduction, plus the location of impeller 58 in close proximity to sparger 26, as well as the position of the tube baffles, all contribute to the extremely high level of oxygen transfer of which the inventive fermentation apparatus is capable. The fermentation vessel of the invention is capable of oxygen transfer rates in the range of at least about 300 millimoles of oxygen per liter per hour (mmol $O_2$/L/hr). In addition, the heat removal capability of the invention fermentation vessel is sufficient to remove the large amounts of heat produced by the fermentation, which large amounts of heat are generated as a result of the high levels of oxygen made available to the fermentation broth. Thus, heat removal on the order of at least about 36 Kcal/liter/hour are possible with fermentation apparatus constructed in accordance with the present invention.

Fermentation vessel 10 is also equipped with means for removing ferment, i.e. port 30. When fermentation is carried out in continuous mode, continuous or intermittent withdrawal of ferment can be accomplished via port 30 while fresh nutrients are provided via inlets 20, 22 and 24.

Fermentation vessel 10 is further equipped with at least one means for degassing foam, e.g., a foam breaker, as for example the foam breaker disclosed by Hunt in U.S. Pat. No. 4,373,024, assigned to Phillips Petroleum Company, or the assembly of elements 60, 62 and 64 illustrated in FIGS. 1 and 2. Cones 62 are mounted on shaft 60 which is rotated by drive means 64. The impact of foaming ferment with rotating cones 62 causes disruption of the foam and causes liquid to return to the main part of the fermentation vessel while gas released from the foam exits the fermentor via line 32. While at least one foam breaker will be employed on the invention fermentation vessel, sufficient foam breaking capacity to handle the amount of foam anticipated from a given fermentation process can be provided by an appropriate number of foam breakers located about the dome portion of the fermentation vessel. Alternatively, a single, high capacity foam breaker can be employed.

Nutrients typically introduced via inlet 20 are substrate, i.e., carbon energy source for the organism being grown in the fermentor, as well as trace minerals, i.e., nutrients required only in small amounts by the organism being grown. Nutrients typically introduced via inlet 22 are the macronutrients, i.e., nutrients required in more substantial amounts by the organism being grown.

The carbon energy substrate can be any carbon energy source, such as hydrocarbons, oxygenated hydrocarbons, including various carbohydrates, and the like, suitable as substrates for microorganisms. It is recognized that particular microorganisms do vary in their preference for various substrates.

The presently preferred substrates for aqueous fermentation at high productivity are the carbon-oxygen-hydrogen significantly water-soluble compounds. The term "oxygenated hydrocarbon" is intended to be a generic term in this disclosure descriptive of compounds employable, and not necessarily a limiting term referring to the source of the substrate. For this disclosure, the oxygenated hydrocarbons include the water-soluble carbohydrates, as well as those alcohols, ketones, esters, acids, aldehydes, and mixtures of any two or more thereof, which are reasonably significantly water-soluble in character; generally compounds having 1 to 20 carbon atoms per molecule. The more suitable oxygenated hydrocarbons are those of substantially greater water-solubility having up to about 12 carbon atoms per molecule, and the water-soluble carbohydrates generally.

Exemplary carbohydrates include glucose, fructose, galactose, lactose, sucrose, starch, dextrin, and the like, alone or in admixture; as well as by-product streams containing assimilable quantities of such carbon sources, such as, for example, whey, whey permeate, cane molasses, beet molasses, and the like. Of the other types of oxygenated hydrocarbons, examples include methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadencanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and the like, as well as mixtures of any two or more thereof.

It also is possible to employ as substrate normal paraffins having about 10 up to 20 carbon atoms per molecule, though such substrate is presently less preferred where single cell protein is the desired product for such use as food because of the difficulty sometimes encountered in removing residual substrate from the microbial cells. These normal paraffins include such as decane, undecane, dodecane, tridecane, tetradecane, pentadecane, hexadecane, octadecane, eicosane, and the like, as well as mixtures of any two or more thereof. Microorganisms generally do not assimilate paraffins of less than 10 carbon atoms per molecule.

Petroleum gases such as methane, ethane, and the like, can be oxidized, and the water-soluble materials employed to provide mixtures predominantly of the corresponding alcohol as well as various aldehydes, ketones, acids, and the like. Similarly, suitable hydrocarbon fractions from various petroleum refinery sources produced within the integrated refining and chemical processing complex, sometimes termed a petro-complex, can be utilized for fermentation purposes.

Nutrients typically introduced via inlet 22 are the macro-nutrients, i.e., minerals required by the organism being grown in the fermentor in relatively large amounts, including, potassium, phosphorus, magnesium, sulfur, and calcium.

Although the composition of the ferment can vary over a wide range, depending in part on the microorganism and substrate employed, the minerals content in the ferment (that is, liquid plus cells) in high productivity fermentation processes is relatively high, at higher levels than heretofore considered suitable or practiced by the prior art. Set forth in Table I below are the minimum, broad, and presently preferred ranges of concentrations of various elements in the ferment, the concentration being expressed as of the element. It is, of course, recognized by those of skill in the art that all or part of each element can be present in the form of a soluble ion, or in cases such as P, are present in a combined form of some type such as phosphate. The amount of each element is expressed in grams or milligrams per liter of ferment (aqueous phase, including cells):

TABLE I

| | Weight of Element per Liter of Ferment | | |
|---|---|---|---|
| Element | Minimum | Broad Range | Preferred Range |
| P | 1.9 g | 2.9–20 g | 2.2–10 g |
| K | 1 g | 1–20 g | 1.5–10 g |
| Mg | 0.15 g | 0.15–3 g | 0.3–1.2 g |
| Ca | 0.06 g | 0.06–1.6 g | 0.08–0.8 g |
| S | 0.1 g | 0.1–8 g | 0.2–5 g |
| Fe | 6 mg | 6–140 mg | 9–80 mg |
| Zn | 2 mg | 2–100 mg | 3–40 mg |
| Cu | 0.6 mg | 0.6–16 mg | 1–10 mg |
| Mn | 0.6 mg | 0.6–20 mg | 0.9–8 mg |

Sulfur desirably is employed in the form of sulfate. Some of the metals required are advantageously added in the form of a sulfate, so that the minimum concentrations of sulfur normally are exceeded. Any or all of the metals listed can be used or present as the sulfate. Preferably, the magnesium, calcium, iron, zinc, copper, and manganese are employed in the form of a sulfate or chloride, or in the form of a compound which is converted in situ to a sulfate or chloride. The potassium preferably is employed as a sulfate, chloride, or phosphate or in the form of a compound which is converted in situ to a sulfate, chloride, or phosphate. The phosphorus preferably is employed in the form of phosphoric acid or in the form of a phosphate, monohydrogen phosphate, or dihydrogen phosphate, e.g., as a potassium or ammonium salt, or as a compound which is converted in situ to such a salt.

Conveniently, a primary mineral salts medium can be employed to include the nutrients comprising P, K, Mg, S, and Ca; and a trace mineral medium can be employed to supply nutrients comprising Fe, Zn, Mn, and Cu.

Other elements which may be present, at least in trace amounts, include such as sodium and cobalt, e.g., as a halide or sulfate; molybdenum, e.g., as molybdate; boron, e.g., as borate; selenium, e.g., as selenite or selenate; or iodine, e.g., as iodide.

In typical high productivity fermentation, the ferment will comprise about one-half supernatant medium and one-half yeast cells, by volume. These one-half by volume yeast cells, however, will contain at least about two-thirds of the mineral salts content of the ferment (liquid plus cells).

In addition to the mineral salts, vitamins (organic growth factors) can be employed in the ferment as is known in the art, when their presence is desirable for the propagation of the particular microorganism chosen. For example, many yeasts for their proper propagation, seem to require the presence of one or both of the vitamins biotin and thiamine, or other medium constituents which contain these vitamins, e.g., yeast extract. Thus, for example, with a yeast such as a *Hansenula polymorpha* it is desirable to employ biotin in an amount of about 0.04 to 0.8 milligram per liter of aqueous mineral medium and thiamine hydrochloride in an amount of about 4 to 80 milligrams per liter of aqueous mineral medium. Alternatively, all or part of the biotin and thiamine can be provided by use of yeast extract or the like.

Yeasts require a source of assimilable nitrogen. The assimilable nitrogen can be supplied by any nitrogen-containing compound or compounds capable of releasing nitrogen in a form suitable for metabolic utilization by the yeast microorganism. While a variety of organic nitrogen source compounds, such as protein hydrolysates, technically can be employed, usually cheaper nitrogen-containing compounds such as ammonia, ammonium hydroxide, urea, nitric acid, and various ammonium salts such as ammonium phosphate, ammonium sulfate, ammonium pyrophosphate, and ammonium chloride can be utilized. Ammonia gas itself is convenient for large scale operations, and can be employed by bubbling through the aqueous microbial ferment in suitable amounts. At the same time, such ammonia also assists in pH control.

The pH range in the aqueous microbial ferment should be in the range of about 3 to 7, more preferably and usually about 3.5 to 5.5 for yeasts. Preferences of certain microorganisms for a pH range are dependent to some extent on the medium employed, as well as on the particular microorganism, and thus may change somewhat with change in medium as can be readily determined by those skilled in the art.

It is known that water containing residual amounts of chlorine tends to render ineffective the growth factors, particularly vitamins such as biotin or thiamine. Such chlorine-containing water can nevertheless be utilized in fermentation processes employing vitamins without inactivation of the vitamins by the chlorine if the vitamins are added to the fermentation zone as a stream separate from the aqueous nutrient medium stream. Thus, there can be employed as the mineral nutrient medium make-up water containing trace amounts of chlorine. This arrangement thus avoids the need for pre-treating, by expensive and/or time consuming methods, the water which contains residual trace amounts of chlorine.

The above-described separate addition of the vitamins to the fermentation zone is preferably and conveniently accomplished by admixing the vitamins with at least a portion of but preferably the entire carbon energy substrate stream prior to charging these materials to the fermentation zone. If an aqueous admixture of vitamins and carbon energy substrate is employed, the water used for initial dilution of the vitamins should preferably be free of traces of residual chlorine, such as deionized water, to avoid any premature loss before mixing with the aqueous carbon substrate stream such as methanol-in-water.

If desired, and also preferred, an admixture can be made of water and a water-soluble carbon substrate such as methanol, such as about 20 volume percent methanol in water, and then the vitamins can be dissolved in the methanol-in-water solution, and fed then to the fermentor. By this mode, residual chlorine need not be first removed, but yet the vitamins are fully preserved.

In a more preferred embodiment, the separate addition of vitamins to the fermentation zone is accomplished utilizing an admixture of vitamins, at least a portion of the carbon energy substrate as noted above, and the further addition of an aqueous trace mineral salts solution. The trace mineral salts comprise what has been referred to hereinabove as the trace elements such as cobalt, molydenum, boron selenium, iodine, as well as manganese, copper, zinc, and iron. The use of this more preferred embodiment not only avoids the vitamin inactivation problem caused by traces of chlorine in the water used for the aqueous mineral salts medium, but also avoids another problem that is often encountered in the fermentation processes. This problem is the formation of precipitates in the heat sterilization zone employed to treat the aqueous mineral salts medium, requiring frequent cleaning. The presence of the trace mineral salts in its usual admixture with the primary mineral nutrient sales apparently promotes the formation of troublesome precipitates in the heat sterilization zone. Thus, by not including the trace mineral salts in the aqueous mineral salts medium stream, but rather instead charging the trace mineral salts in admixture with the vitamins and at least a portion of the carbon energy substrate, two very troublesome problems are solved. As noted above, the water used to prepare the admixture of trace mineral salts, at least a portion of the carbon energy substrate, and the vitamins should preferably be free of residual traces of chlorine.

The stream comprised of vitamins, a portion of the carbon energy substrate, and trace minerals can be sterilized by filtration if desired. However, it is preferable and convenient to combine said stream with the major carbon energy substrate stream prior to charging to the fermentation zone and filtering the entire combined streams just prior to charging to the fermentation zone.

The fermentation itself is an aerobic aqueous process requiring molecular oxygen which is supplied by a molecular oxygen-containing gas such as air, oxygen-enriched air, or even substantially pure molecular oxygen, so as to maintain the ferment with an oxygen partial pressure effective to assist the microorganism species in growing or in biochemically converting substrate in a thriving fashion. By using an oxygenated hydrocarbon substrate, the total oxygen requirements for growth or substrate conversion of the microorganism are reduced from the requirements when a paraffin is used. Even so, adequate quantities of molecular oxygen must be supplied for growth, since the assimilation and/or bioconversion of the substrate and corresponding growth of the microorganism is, in part, a combustion process.

The pressure employed for the microbial fermentation step can range widely. Typical pressures are about 0 to 150 psig, presently preferably about 0 to 60 psig, more preferably 35 to 40 psig, as a balance of equipment and operating costs versus oxygen solubility achieved. Greater than atmospheric pressures are advantageous in that such pressures do tend to increase the dissolved oxygen concentration in the aqueous ferment, which in turn can help increase cellular growth rates. At the same time this is counterbalanced by the fact that high pressures do increase equipment and operating costs.

The following non-limiting example further illustrates the advantages of the fermentation vessel of the present invention.

EXAMPLE

This example describes the oxygen transfer rates and heat transfer coefficients obtained during fermentations carried out in both a prior art fermentor, containing plate baffles for cooling, and a fermentor constructed in accordance with the present invention.

The fermentation vessel, before and after modification, had a shell with an overall height of 92.32 inches and an internal diameter of 34.8 inches and a total working volume of about 1500 liters. Before modification, the prior art fermentation vessel was equipped with two 10 inch diameter, 6-blade Rushton-type turbines having a blade height of 1.5 inches. The turbines were located 12 15/16 inches and 47 inches above the bottom of the fermentor bottom. The prior art fermentation vessel was also equipped with 16 plate baffles each 56.6 inches long and 7 inches wide. The baffles were spaced equally around the circumference of the fermentation vessel, and projected radially toward the axis of the central drive shaft.

The prior art fermentation vessel was also equipped with a 9.5 inch outer diameter sparge ring made from one inch stainless steel tubing and containing sixteen (16) 13/64 inch diameter holes. The sparge ring was positioned about 2 inches below the bottom-most part of the mixer blades of the lower turbine.

In the invention fermentor, all 16 of the original plate baffles were removed and replaced with 3-tube baffles spaced approximately evenly around the fermentor circumference, and canted 15° toward the direction of fluid flow. Each tube baffle contained twelve (12) $\frac{3}{4}$ inch diameter stainless steel tubes with 0.065 inch walls. The twelve tubes were arranged in two banks of six tubes each. The spacing between the tubes in each bank was one tube diameter, with the tube center of one bank off-set one-half of the tube diameter from the tubes in the adjacent bank. The tube baffles were 62 13/16 inches high by 9 inches wide by 3.1 inches thick. The spacing between the fermentor wall and the tube baffles was 1.25 inches while the spacing between the bottom of the tube baffles and the fermentor bottom was 10 1/16 inches.

In addition, the fermentation vessel was equipped with 21 solid plate baffles, each 61.25 inches high by 9 inches wide and 12 gage thick. The plate baffles were canted 15° toward the direction of fluid flow. The plate baffles were positioned 10 3/8 inches above the fermentor bottom and the plates were spaced 1.25 inches from the fermentor wall.

Both fermentors were employed for growth of *Pichia pastoris* on methanol, as follows:

In a continuous aerobic fermentation process, methanol and an aqueous mineral medium in a volume ratio of 40 to 60, respectively, were fed individually to a fermentor inoculated with the yeast species *Pichia pastoris* Culture 21-1 deposited as NRRL Y-11430. The fermentor was a 1500-liter foam-filled fermentor with a liquid volume of about 600 liters, with automatic pH, temperature, and level control. Agitation was provided by a turbine driven at 1050 rpm. The aeration rate was about 6.1 up to 6.3 normal volumes of air (at about 1 atm and about 0° C.) per volume of ferment in the fermentor per minute. Anhydrous ammonia was added at a rate to maintain the pH of the ferment mixture at about 3.5.

The primary aqueous mineral salts medium was prepared by mixing, for each liter of solution, 12.2 mL 75 percent $H_3PO_4$, 6.0 g KCl, 6.0 g $MgSO_4.7H_2O$, 0.8 g $CaCl_2.2H_2O$, 2.0 g 85 percent KOH, 2.0 mL of trace mineral solution, 0.8 mL of a biotin-thiamine hydrochloride solution, and sufficient tap water to make 1 liter of solution, the tap water first having been treated with enough sodium thiosulfate to react with the free chlorine present therein.

Trace mineral solution was prepared by mixing, for each liter of solution, 67.5 g $FeCl_3.6H_2O$, 18 g $ZnSO_4.7H_2O$, 5.0 g $MnSO_4.H_2O$, 6.0 g $CuSO_4.5H_2O$, 2.0 mL conc. $H_2SO_4$, and sufficient deionized water to make 1 liter of solution.

The biotin-thiamine hydrochloride solution was made by mixing the components in the ratio of 0.4 g biotin to 40 g thiamine hydrochloride to 1 liter deionized water.

The fermentation was conducted at 30° C. and 8 to 10 psig pressure, with a retention time of about 20 hours.

The reaction parameters and resulting oxygen transfer rates and heat transfer coefficients achieved with the two above-described fermentors are summarized in Table II.

TABLE II

| | Baffle Type | |
|---|---|---|
| | Plate | Tube |
| Gas Rate, NCuM/hr* | 239.8 | 227.2 |
| Gas Velocity, Ft/s | 0.250 | 0.222 |
| Pressure, psig | 8 | 9.5 |
| Liquid Volume, L | 636.5 | 625.2 |
| Mixer Speed, rpm | 1050 | 1050 |
| Mixer Power, KW (net) | 10.9 | 10.4 |
| Oxygen Transfer Rate, mmole $O_2$/L/hr | 487.8 | 526.0 |
| Heat Removed, 100,000 BTU/hr | | |
| Jacket | 0.45 | 0.51 |
| Baffles | 1.28 | 1.19 |
| Total | 1.73 | 1.70 |
| Heat Transfer Coefficient, BTU/hr/ft$^2$/°F. | | |
| Jacket, Overall | 61.6 | 58.7 |
| Baffles, Overall | 114.7 | 199.9 |
| Baffles, Biofluid | 161.5 | 289.9 |

*Normal cubic meters per hour.

The above data illustrate the higher overall heat transfer coefficient (199.9 v. 114.7) and biofluid heat transfer coefficient (289.9 v. 161.5) obtained from the use of tubular baffles orientated at an angle of 15° from the radius compared to the use of axially oriented plate baffles.

In addition, the oxygen transfer rate appears to be higher (526 v. 488) as a result of the fermentor modification.

The example has been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

That which is claimed is:

1. A fermentation apparatus comprising:
    (a) a fermentor vessel shell having a hollow interior chamber adapted to contain fluid therein, said vessel having upper and lower end portions and an inner and outer vessel diameter;
    (b) heat exchange means disposed in said vessel, wherein said heat exchange means comprises a plurality of baffles, wherein each of said baffles comprise a plurality of parallel tubes, each of which tubes having a first end and a second end, wherein each of said baffles is equipped with
        (i) an inlet header means for introducing heat exchange fluid into each of said baffles, in open communication with the first end of said parallel tubes, and
        (ii) an outlet header means for removing heat exchange fluid from each of said baffles, in open communication with the second end of said parallel tubes;
    wherein the plurality of baffles are positioned within said vessel so as to define an inner heat exchange diameter and an outer heat exchange diameter wherein said inner heat exchange diameter defines an unobstructed zone occupying in the range of about 30 up to 60% of the total internal fermentor vessel diameter and said outer heat exchange means diameter is no greater than the inner diameter of said vessel; wherein the axis of the parallel tubes of said plurality of baffles is parallel to the longitudinal axis of said fermentor vessel; wherein each of said plurality of baffles is positioned at an angle, $\alpha$, with respect to the radial projection from the longitudinal axis of the fermentation vessel to the point where the longitudinal axis of the parallel tube rows intersects the inner diameter of the vessel, wherein $\alpha$ ranges from 5° up to 30°;
    (c) first inlet means for the introduction of nutrient media and carbon and energy source into said fermentor vessel;
    (d) agitation means comprising
        (i) a shaft centrally positioned within said fermentor vessel and coaxially aligned with the longitudinal axis of said fermentor vessel,
        (ii) drive means attached to said shaft, and
        (iii) a plurality of impellers mounted on said shaft; wherein the diameter of said impellers is no greater than the unobstructed zone defined by the inner heat exchange diameter; wherein at least the bottom-most impeller is mounted on said stirring shaft in the lower end portion of said vessel;
    (e) second inlet means for the introduction of gas into said fermentor vessel comprising a sparging means having a face side with a plurality of holes therein; wherein said sparging means is positioned symmetrically in the fermentor vessel with respect to the longitudinal axis of said fermentor vessel; wherein the diameter of said sparging means is no greater than the diameter of said impellers; and wherein the face side of said sparging means is positioned parallel to, and within ⅛ to 1/10 impeller diameters from, the bottom edge of the bottom-most impeller of said plurality of impellers;
    (f) outlet means for the removal of ferment from the lower end portion of said fermentor vessel; and
    (g) means for degassing foam mounted on the upper portion of said fermentor vessel and positioned on the outer perimeter thereof.

2. Apparatus in accordance with claim 1 wherein said angle, $\alpha$, ranges from 10° up to 20°.

3. Apparatus in accordance with claim 1 wherein said plurality of baffles ranges in number from 2 up to 30 baffles.

4. Apparatus in accordance with claim 1 wherein said parallel tubes range in length from 25 up to 90% of the longitudinal vessel length of said fermentor vessel.

5. Apparatus in accordance with claim 1 wherein said parallel tubes contain at least one U-shape bend such that the first and second ends of the parallel tubes of said baffles are adjacent to one another.

6. Apparatus in accordance with claim 1 wherein the space between said parallel tubes ranges between about 0.5 up to 4 tube diameters.

7. Apparatus in accordance with claim 1 wherein said plurality of baffles consists of in the range of 4 up to 24 baffles.

8. Apparatus in accordance with claim 1 wherein said baffles each comprise an assembly of 1 up to 6 parallel rows of tubes.

9. Apparatus in accordance with claim 8 wherein the space between said parallel rows of tubes ranges between about 0.5 up to 4 tube diameters.

10. Apparatus in accordance with claim 4 wherein said parallel tubes comprise a plurality of stacked cooling baffles, each of which is shorter than the total parallel tube length.

11. Apparatus in accordance with claim 1 wherein said fermentation vessel has a vessel length to diameter ratio in the range of 0.1:1 up to 10:1.

12. Apparatus in accordance with claim 1 wherein said plurality of impellers ranges in number from 2 up to 12.

13. Apparatus in accordance with claim 1 wherein said bottom-most impeller comprises a disc having mounted thereon a plurality of blades, wherein said blades are positioned perpendicular to the plane of the disc and on a radial projection from the vertical axis of said disc.

14. Apparatus in accordance with claim 1 wherein the outer heat exchange means diameter varies in the range of about 90 up to 98% of the total inner vessel diameter.

15. Apparatus in accordance with claim 1 further comprising a second inlet means for the introduction of nutrient media and carbon and energy source.

16. Apparatus in accordance with claim 1 wherein said drive means is positioned outside the outer vessel diameter and at the upper end portion of said vessel.

17. Apparatus in accordance with claim 1 wherein said drive means is positioned outside the outer vessel diameter and at the lower end portion of said vessel.

18. Apparatus in accordance with claim 1 wherein each of said inlet header means are attached to a supply header means in open communication therewith.

19. Apparatus in accordance with claim 17 wherein said supply header means is positioned outside the fermentor vessel.

20. Apparatus in accordance with claim 1 wherein each of said outlet header means are attached to a collector header means in open communication therewith.

21. Apparatus in accordance with claim 20 wherein said collector header means is positioned outside the fermentor vessel.

* * * * *